United States Patent [19]

Klueppel et al.

[11] Patent Number: 4,820,507
[45] Date of Patent: Apr. 11, 1989

[54] ORAL AND DENTAL HYGIENE PREPARATIONS

[75] Inventors: Hans-Juergen Klueppel, Duesseldorf; Walter Ploeger, Hilden; Horst Rutzen, Langenfeld; Rudolf Lehmann, Leichlingen, all of Fed. Rep. of Germany

[73] Assignee: Henkel Kommanditgesellschaft auf Aktien, Duesseldorf, Fed. Rep. of Germany

[21] Appl. No.: 18,762

[22] Filed: Mar. 2, 1987

Related U.S. Application Data

[63] Continuation of Ser. No. 672,425, Nov. 16, 1984, abandoned.

[30] Foreign Application Priority Data

Dec. 17, 1983 [DE] Fed. Rep. of Germany ....... 3345781

[51] Int. Cl.$^4$ .......................... A61K 7/22; A61K 7/16; A61K 7/24
[52] U.S. Cl. ...................... 424/54; 424/49; 424/57; 424/55; 514/900; 514/901; 514/835
[58] Field of Search ...................... 424/49, 54, 55, 57; 514/900–901, 835

[56] References Cited

U.S. PATENT DOCUMENTS 3,277,118 10/1966 Schmid et al. ............... 260/347.7
3,369,046 2/1968 Kaniecki ............... 424/54
3,488,419 1/1970 McCune et al. ............... 424/49
3,703,583 11/1972 Martin ............... 424/54
3,988,443 10/1976 Plöger ............... 514/91
4,492,802 1/1985 Rutzen et al. ............... 564/292

FOREIGN PATENT DOCUMENTS 673101 10/1963 Canada .
3116087 11/1982 Fed. Rep. of Germany .
1394172 5/1975 United Kingdom .

Primary Examiner—Margaret Moskowitz
Assistant Examiner—F. T. Moezie
Attorney, Agent, or Firm—Ernest G. Szoke; Wayne C. Jaeschke; Henry E. Millson, Jr.

[57] ABSTRACT

Oral and dental hygiene preparations containing quaternary ammonium compounds of the formula

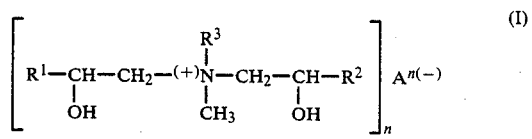

wherein $R^1$ is an n-alkyl group, preferably containing from 8 to 12 carbon atoms, $R^2$ is hydrogen, a $CH_3$-group or a $CH_2OH$-group and $R^3$ is a $CH_3$-group or a group of the formula $-CH_2-CH(OH)-R^2$, A is an inorganic or organic acid anion and n is the basicity of the anion. The quaternary ammonium compounds of formula I can have a plaque inhibiting effect and show only slight antimicrobial activity. $R^1$ is preferably an n-decyl group, $R^2$ is hydrogen and $R^3$ is a $CH_3$-group or a 2-hydroxyethyl group. The oral and dental hygiene preparations also preferably contain fluorides and/or organophosphonates as the anion A.

34 Claims, 2 Drawing Sheets

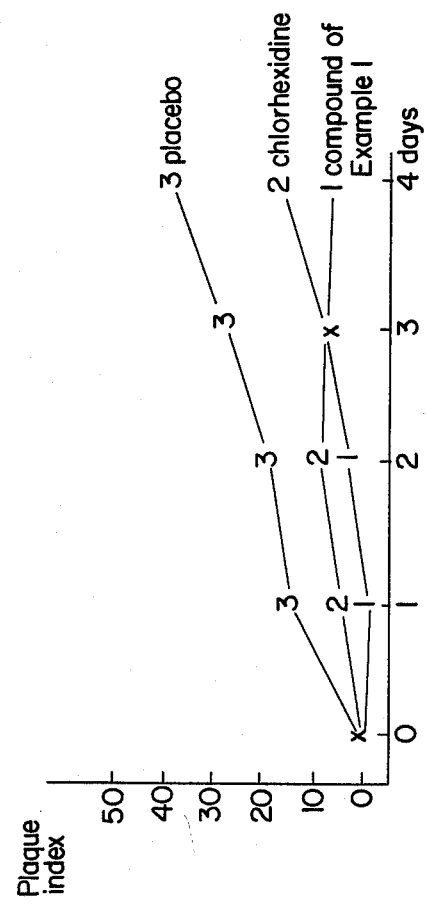

ORAL AND DENTAL HYGIENE PREPARATIONS

This application is a continuation of application Ser. No. 672,425, filed Nov. 16, 1984, now abandoned.

BACKGROUND OF THE INVENTION

1. Field of the Invention

This invention relates to oral and dental hygiene preparations containing plaque-preventing quaternary ammonium compounds.

2. Description of the Relevant Art

Oral and dental hygiene preparations are products used to clean and care for the oral cavity, the teeth and the throat.

In addition to cleaning teeth to remove dental coatings (so-called "dental plaque"), the function of oral and dental hygiene preparations is to stop the formation of tartar and to prevent dental disorders, such as caries and periodontosis, and also to eliminate halitosis.

A central problem is the removal of dental coatings. Measures which reduce plaque formation or which remove already formed coatings lead to a reduction in both periodontopathias and caries. Accordingly, one of the objects of the present invention is to provide oral and dental hygiene preparations which are active against the formation of dental coatings.

Plaque formation can be reduced by using microbicidal substances in oral and dental hygiene preparations. Examples include chlorhexidine (1,1'-hexamethylene-bis[5-(4-chlorophenyl)-biguanide]) and numerous antibacterially active quaternary ammonium compounds, such as cetyl pyridinium chloride or the quaternary ammonium compounds described in U.S. Pat. No. 3,369,046. Unfortunately, such antimicrobial compounds can quite indiscriminately attack all the microflora in the oral cavity and thus cause or promote disease of the oral cavity. Such microbicides can also cause serious irritation of the mucous membrane. Another disadvantage of most of the quaternary ammonium compounds is that they can discolor the teeth.

Canadian Pat. No. 673,101 describes the use of a variety of quaternary ammonium fluorides to reduce the solubility of dental enamel in acids. Such compounds either disadvantageously have a strong antimicrobial effect, as explained above, or are ineffectual in preventing plaque.

Accordingly, another object of the present invention is to provide substances which, in oral and dental hygiene preparations, are highly effective against the formation of plaque but which show hardly any antimicrobial activity.

BRIEF DESCRIPTION OF THE DRAWINGS

FIG. 3 shows the inhibition of plaque growth by a compound of the invention compared to a placebo and chlorhexidine.

DESCRIPTION OF THE INVENTION

Figure 1:
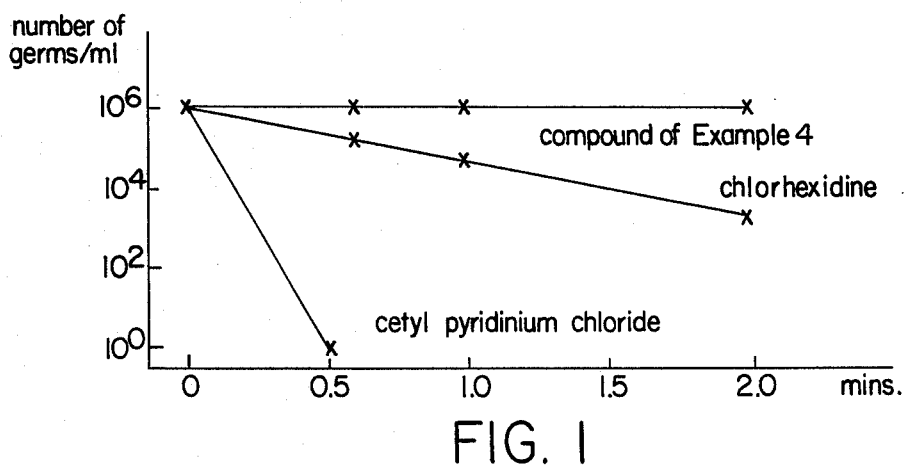
FIGS. 1 and 2 show the destruction of Streptococcus mutans by a compound of the invention compared to reference compounds.

It has surprisingly been found that oral and dental hygiene preparations containing quaternary ammonium compounds corresponding to the following formula (I) can achieve the objects of the invention:

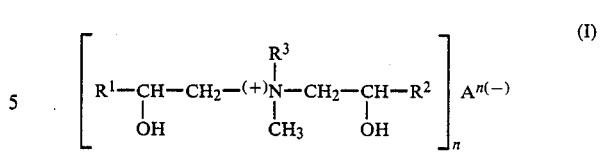

in which $R^1$ is an n-alkyl group, preferably containing from 8 to 12 carbon atoms, $R^2$ is hydrogen, a $CH_3$-group or an $HO-CH_2$-group, and $R^3$ is a $CH_3$-group or a group of the formula $-CH_2-CH(OH)-R^2$, A is a physiologically compatible inorganic or organic acid anion and n represents the basicity of the anion.

Even when used in low concentrations in oral and dental hygiene preparations, the quaternary ammonium compounds corresponding to the formula I show pronounced plaque-preventing activity which exceeds that of typical antimicrobial agents such as, for example, chlorhexidine. The compounds of formula I, moreover, show very little antimicrobial activity in general and, in effective plaque-inhibiting concentrations, show substantially no antimicrobial activity. In clinical trials, quaternary ammonium compounds of formula I did not cause any discoloration of teeth.

Regarding the alkyl group $R^1$, those compounds of formula I wherein $R^1$ is an n-decyl group show optimum performance properties. Although the plaque-preventing effect increases as the chain length of $R^1$ increases, so does the undesirable antimicrobial effect. There is no antimicrobial effect when $R^1$ is an alkyl of less than 8 carbon atoms; however, the plaque-preventing effect is weakened.

$R^2$ is preferably hydrogen and $R^3$ is preferably a methyl or 2-hydroxyethyl group. Accordingly, particularly suitable compounds corresponding to formula I are the 2-hydroxydodecyl-2-hydroxyethyldimethyl ammonium salts and the 2-hydroxydodecyldi(2-hydroxyethyl)methylammonium salts.

The anion used may be any physiologically compatible inorganic or organic acid ion which forms a water-soluble salt with the quaternary ammonium ion. Representative inorganic acid anions include halides, particularly fluoride, chloride, or bromide, sulfates or hydrogen sulfates, phosphates, hydrogen phosphates, nitrates, borates, carbonate and hydrogen carbonates.

Representative organic acid anions include formate, acetate, propionate, lactate, glycolate, citrate, tartrate, malate, malonate, maleate, succinate, gluconate, benzoate, salicylate, sorbate, ascorbate, etc.

By virtue of the known anti-caries properties of dissolved fluoride, oral and dental hygiene preparations in accordance with the present invention containing quaternary ammonium compounds of formula I in which $A^{(-)}$ is a fluoride anion are particularly preferred. Another preferred embodiment of the invention comprises oral and dental hygiene preparations containing quaternary ammonium compounds of the formula I in which A is an organophosphonate anion.

The salts of organophosphonic acids are particularly suitable because the organophosphonates have been disclosed to show tartar-inhibiting effects, as seen in U.S. Pat. No. 3,488,419 and U.S. Pat. No. 3,988,443, each of which is specifically incorporated in its entirety by reference herein, and also in Great Britain patent specification No. 1,394,172.

Organophosphonic acids corresponding to the formula II or III below are preferred:

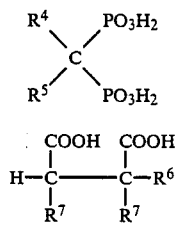

(II)

$$\text{H}-\underset{\underset{R^7}{|}}{\overset{\overset{COOH}{|}}{C}}-\underset{\underset{R^7}{|}}{\overset{\overset{COOH}{|}}{C}}-R^6 \quad (III)$$

in which $R^4$ is an alkyl group containing from 1 to 6 carbon atoms, a hydroxyl group, an amino group, a group of the formula —$NHR^8$, wherein $R^8$ is an alkyl group containing from 1 to 3 carbon atoms, a group of the formula —$CH_2$—COOH, —$CH_2PO_3H_2$, —$CH_2$—$CH_2$—$PO_3H_2$, —$CH(PO_3H_2)$ (OH) or —$CH_2$—$CH$—$(PO_3H_2)_2$; $R^5$ is hydrogen, an alkyl group containing from 1 to 6 carbon atoms or, where $R^4$ is an amino group or an —$NHR^8$ group, forms a 5- to 7-membered azacycloalkane ring with the nitrogen atom and the central carbon atom; $R^6$ is a group of the formula —$PO_3H_2$, $CR^7(COOH)(PO_3H_2)$, $CR^7(PO_3H_2)_2$ or $CR^7(COOH)$ —$CH_2$—$PO_3H_2$; and $R^7$ is hydrogen, an alkyl group containing from 1 to 4 carbon atoms, more particularly a —$CH_3$ group, or a —$(CH_2)_{1-2}$—COOH group.

Phosphonoalkanepolycarboxylic acids which correspond to the general formula III are, for example, 1-phosphonoethane-1,2-dicarboxylic acid, 2-phosphonopropane-2,3-dicarboxylic acid, 2-phosphonobutane-2,3-dicarboxylic acid, 1-phosphonopropane-1,2-dicarboxylic acid, 1-phosphonopropane-1,2,3-tricarboxylic acid, 1-phosphonobutane-2,3,4-tricarboxylic acid, 2-phosphonobutane-2,3,4-tricarboxylic acid, 1-phosphonobutane-1,2,3-tricarboxylic acid, 2-phosphonopentane-2,3,4-tricarboxylic acid, 1-phosphono-2-methylpropane-1,2,3-tricarboxylic acid, 2-phosphono-3-methylbutane-2,3,4-tricarboxylic acid, 2-phosphono-3-methylpentane-2,3,4-tricarboxylic acid, 1-phosphono-2-methylbutane-1,2,3-tricarboxylic acid, 1,1-diphosphonopropane-2,3-dicarboxylic acid, 1,1-diphosphonobutane-2,3-dicarboxylic acid, 2,2-diphosphonobutane-3,4-dicarboxylic acid, 2,2-diphosphonopentane-3,4-dicarboxylic acid, 1,1-diphosphono-2-methylpropane-2,3-dicarboxylic acid, 1,1-diphosphono-2-methylbutane-2,3-dicarboxylic acid, 2,2-diphosphono-3-methylbutane-3,4-dicarboxylic acid and 2,2-diphosphono-3-methylpentane-3,4-dicarboxylic acid.

1-Phosphonoethane-1,2-dicarboxylic acid can be prepared by reaction of a maleic acid ester with diethyl phosphite in the presence of sodium alcoholate and subsequent acid saponification of the ester. 2-Phosphonopropane-2,3-dicarboxylic acid may be obtained in a similar way, but before the saponification, reaction with methyl chloride is effected.

1-Phosphonopropane-1,2,3-tricarboxylic acid may be prepared by reaction of a maleic acid ester with a phosphonoacetic acid ester in the presence of an alcoholate and subsequent saponification of the ester obtained. The preparation of 1-phosphonobutane-2,3,4-tricarboxylic acid may be carried out by reaction of dimethyl phosphite with 1-butene-2,3,4-tricarboxylic acid ester in the presence of sodium alcoholate and subsequent saponification of the resulting ester to the desired acid. An ester is obtained, which is converted by acid hydrolysis into 1,1-diphosphonopropane-2,3-dicarboxylic acid by reaction of methanediphosphonoacid alkyl esters with maleic acid alkyl esters in the presence of sodium alcoholate.

2-Phosphonobutane-2,3,4-tricarboxylic acid may be obtained by reaction of α-diethylphosphonopropionic acid-methyl ester with diethyl maleate in the presence of an alcoholate and subsequent saponification of the ester obtained.

The preparation of 2,2-diphosphonobutane-3,4-dicarboxylic acid is effected by reacting a maleic acid ester with an ethane-1,1-diphosphono-acid ester in the presence of sodium alcoholate and subsequent acid saponification of the product obtained.

The further phosphonoalkanepolycarboxylic acids are obtained by analogous methods, in which, particularly, citraconic acid ester is used instead of maleic acid ester.

The quaternary ammonium compounds corresponding to the formula I may be obtained by those of ordinary skill in the art without undue experimentation. For example, they may be produced by the process described by H. Rutzen in Fette, Seifen, Anstrichmittel 84 (1982), pages 87–92, in which tertiary amine salts are quaternized with long-chain 1,2-epoxides. Using this method, the quaternary ammonium compounds used in accordance with the invention may be obtained from the quaternization of salts corresponding to the formula

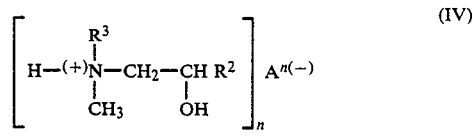

in which $R^2$, $R^3$, A and n have the same meanings as in formula I, with 1,2-epoxides corresponding to the formula

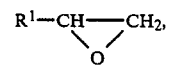

in which $R^1$ has the same meaning as in formula I.

Aqueous solutions of the salts corresponding to general formula IV are prepared by reacting the tertiary amines, for example dimethyl ethanolamine, methyl diethanolamine, or dimethyl-2,3-dihydroxypropylamine, with inorganic or organic acids, such as hydrochloric acid, hydrofluoric acid, sulfuric acid, citric acid, glycolic acid, lactic or organophosphonic acids corresponding to the formula II or III, set forth above, such as 1-hydroxyethane-1,1-diphosphonic acid or 1-phosphonopropane-1,2,3-tricarboxylic acid, in aqueous solution. Particularly favorable conditions for the quaternization reaction are described, for example, in German Application No. 31 16 087, which corresponds to South African Patent Application No. 822757.

The process described in South African Patent Application No. 822757 is carried out by reacting a compound containing a terminal epoxide group with a salt of a tertiary amine in the presence of a quaternary ammonium compound which acts as a catalyst for the reaction. More specifically, the salt of the tertiary amine which is to be reacted with the epoxide compound is preferably dissolved in water prior to use. The aqueous solution of the tertiary amine salt can be prepared either by dissolving the salt to be used in sufficient amounts of water, or by forming the salt by adding an equivalent amount of acid to an aqueous solution of the tertiary amine. The tertiary amine salt solution is then reacted with the epoxide compound in the presence of a quaternary ammonium compound as a catalyst. Useful reaction temperatures are in the range of from about 40° to about 100° C., with a temperature in the range of about 80° to about 95° C. being preferred.

As further described in South African No. 822757, the amount of catalyst to be added to the aqueous solution is from about 0.5 to about 10 wt.%, based on the theoretical weight of the end product. The optimum quantity of catalyst is somewhat dependent on the choice of the epoxide and the amine salt reactants, and the optimum weight of catalyst can be readily determined by simple preliminary experiments. The epoxide compound and the tertiary amine salt are preferably reacted in an approximately equivalent relationship, and more preferably in a relationship of 1 equivalent of epoxide compound to about 1.1 equivalent of tertiary amine salt.

The oral and dental hygiene preparations according to the invention containing quaternary ammonium compounds of the formula I may be in any of the various forms normally used for products of this type, such as mouthwashes, toothpastes or tooth powders. A preparation in accordance with the invention contains at least one of the quaternary ammonium compounds of formula I in an amount effective to inhibit the formation of plaque. Preferably, the compound of formula I should be present in an amount effective to inhibit the formation of plaque without (1) attacking all the microflora in the oral cavity, (2) substantially irritating the mucous membrane; and (3) discoloring the teeth. One of ordinary skill in the art can select an effective amount of the quaternary ammonium compounds of formula I without undue experimentation.

More specifically, the preparation in accordance with the present invention should contain from 0.01% to 2.0% by weight of the quaternary ammonium compounds. To obtain satisfactory plaque prevention, concentrations of from 0.03 to 0.3% by weight are particularly preferred for mouthwashes to be used in undiluted form, whereas concentrations of from 0.1 to 0.5% by weight of the preparation as a whole are particularly preferred for toothpastes. For mouthwash concentrates which are diluted for use, it will be necessary to use higher concentrations which can be readily calculated in accordance with the prescribed dilution ratio.

In addition, oral and dental hygiene preparations in accordance with the invention may also be in the form of chewing gum, oral lozenges and dental care ointments. Quaternary ammonium compounds corresponding to the formula I may also be added to oral hygiene preparations which may have to be applied several times a day and are inevitably swallowed. In cases such as these, however, the dosage of the quaternary ammonium compounds should not exceed 0.1% by weight of the preparation.

In addition to the quaternary ammonium compounds of formula I, the oral and dental hygiene preparations according to the invention may contain any of the additives and carriers normally used.

For mouthwashes, the oral and dental hygiene preparations according to the invention may readily be combined with aqueous-alcoholic solutions containing different amounts of ethereal oils, emulsifiers, astringent and toning drug extracts, caries-inhibiting additives and flavor correctants. One of ordinary skill in the art can readily select appropriate amounts of these ingredients without undue experimentation.

In selecting the emulsifiers and wetting agents to be used, nonionic and ampholytic or zwitter-ionic surfactants are preferred, because anionic surfactants, for example soaps and alkyl sulfates, are capable of detrimentally affecting the plaque-inhibiting effect of the quaternary ammonium compounds of formula I. Preferably, nonionic emulsifiers and wetting agents are used such as ethoxylated sorbitan fatty acid esters, ethoxylated glycerol fatty acid esters, alkyl glucosides, fatty alcohol polyglycol esters, ethylene oxide-propylene oxide block polymers and amine oxides. Of note, the quaternary ammonium compounds of formula I are themselves surfactants.

Toothpastes or tooth creams are generally understood to be paste-like preparations of water, thickeners, humectants, abrasives or polishes, surfactants, sweeteners, flavorings, deodorizing agents and agents active against oral and dental diseases. One of ordinary skill in the art can readily select appropriate amounts of these ingredients to be combined with the quaternary ammonium compounds of formula I without undue experimentation.

In toothpastes according to the invention, any of the usual polishes may be used, such as chalk, dicalcium phosphate, insoluble sodium metaphosphate, aluminium silicates, calcium pyrophosphate, finely particulate synthetic resins, silicas, aluminium oxide and aluminium oxide trihydrate. If the quaternary ammonium compounds of formula I are employed in the form of salts of organophosphonic acids, it is advisable to use polishes which are free from soluble calcium to ensure that the tartar-inhibiting effect of the organophosphonates is not impaired.

Particularly suitable polishes for toothpastes according to the invention are finely particulate xerogel silicas, hydrogel silicas, precipitated silicas, aluminium oxide trihydrate and finely particulate α-alumina, or mixtures of these polishes. Such polishes are preferably used in quantities of from about 15 to 40% by weight of the toothpaste.

Preferred humectants used for toothpastes according to the invention include low molecular weight polyethylene glycols, glycerol, sorbitol or mixtures thereof in quantities of up to about 50% by weight of the toothpaste.

Among the known thickeners for use with toothpastes according to the invention, particularly preferred are the thickening, finely particulate gel silicas and nonionic hydrocolloids, such as hydroxy ethyl cellulose, hydroxy propyl guar, hydroxy ethyl starch, polyvinyl pyrrolidone, high molecular weight polyethylene glycol and vegetable gums, such as tragacanth, agaragar, carrageen moss, gum arabic and xanthan gum. Anionic hydrocolloids are to be used with caution because they detrimentally affect the plaque-inhibiting effect of the quaternary ammonium compounds of formula I.

Although the quaternary ammonium compounds of formula I are themselves surfactants, other surfactants, preferably from the group of nonionic surfactants mentioned above and also zwitter-ionic and amphoteric surfactants, may be added to the toothpastes of the present invention.

The desired flavor and aroma for preparations in accordance with the invention may be obtained by adding the usual ethereal oils, such as peppermint, clove oil, wintergreen oil, sassafras oil, and also sweeteners, such as saccharin, cyclamate, dulcin, dextrose, levulose, etc. If the quaternary ammonium compounds used in accordance with the invention are not already present in the dental hygiene preparations in the form of fluorides or organophosphonates, it is also possible to introduce these caries inhibitors into the oral and dental hygiene preparations in the form of, for example, alkali fluorides, alkali monofluorophosphates or alkali salts of organophosphonic acids, particularly those corresponding to formulae II and III.

In addition, the oral and dental hygiene preparations according to the invention may contain other standard auxiliaries, such as dyes, preservatives and opacifiers, for example titanium dioxide.

The present invention is illustrated by the following examples, which are merely illustrative without being limitative in any manner.

EXAMPLE 1

Production of 2-hydroxydodecyl-2-hydroxyethyl dimethyl ammonium fluoride 44.57 g of dimethyl ethanolamine (0.5 mole) were diluted with 420.65 g of water, followed by the addition of 19.38 g of an aqueous 41.3% hydrofluoric acid solution (0.4 mole). A clear solution was formed. After the solution had been heated to 95° C., 94.0 g of 1,2-epoxydodecane (0.5 mole) and 3.5 g of a 75% dispersion of distearyl dimethyl ammonium chloride (as phase transfer catalyst) were added, after which the reaction mixture was stirred for 6 hours at 95° C. Finally, another 4.84 g of the 41.3% hydrofluoric acid solution (0.1 mole) were added. A clear yellow solution of the 2-hydroxydodecyl-2-hydroxyethyl dimethyl ammonium fluoride containing 73.1 m vals of quaternary ammonium compound (QUAT) per 100 g of the aqueous solution was obtained.

EXAMPLE 2

Production of 2-hydroxydodecyl-di-(2-hydroxyethyl)-methyl ammonium fluoride

A slightly clouded solution of 2-hydroxydodecyl-di-(2-hydroxyethyl)-methyl ammonium fluoride containing 146.8 m vals of quaternary ammonium compound (QUAT) per 100 g of the aqueous solution was obtained as in Example 1 from 66.5 g of methyl diethanolamine (98.5%), 24.2 g of aqueous hydrofluoric acid (41.3%), 94.0 g of 1.2-epoxy-dodecane, 137.0 g of water and 7.0 g of distearyl dimethyl ammonium chloride (75%) in a reaction carried out over a period of 19 hours at 95° C.

EXAMPLE 3

Production of tris-{2-hydroxydodecyl-2-hydroxyethyl-dimethylammonium}-1-hydroxyethyl-1,1-diphosphonate 49.02 g of dimethyl ethanolamine (0.55 mole) were diluted with 483.85 g of water, followed by the addition of 57.35 g of a 60% aqueous solution of 1-hydroxyethane-1,1-diphosphonic acid (0.167 mole). After the addition of 94.0 g of 1,2-epoxydodecane (0.5 mole) and 3.5 g of a 75% dispersion of distearyl dimethyl ammonium chloride, the reaction mixture was heated to 95° C. and stirred for 6 hours, resulting in the formation of a clear yellow solution containing 72.0 m vals of tris-{2-hydroxydodecyl-2-hydroxyethyl-dimethyl-ammonium}-1-hydroxyethyl-1,1-diphosphonate per 100 g of solution.

EXAMPLE 4

Production of 2-hydroxydodecyl-2-hydroxyethyl dimethyl ammonium chloride 338.03 g of an aqueous 37% hydrochloric acid solution were added dropwise under nitrogen to 382.03 g of dimethyl ethanolamine (4.28 moles), 1046.19 g of water and 805.76 g of 1,2-epoxydodecane (4.28 moles). The solution was then heated while stirring to 90° C. in a water bath. After 1 hour, two phases had formed and, after another 20 minutes, the viscosity of the reaction mixture rose appreciably. After stirring for 2.5 hours, the reaction mixture had an epoxide number of 0.05 (% by weight of epoxide oxygen). Another 84.51 g of the 37% hydrochloric acid solution were then added, as a result of which the reaction mixture became thinly liquid again.

After the addition of 665 ml of toluene, 665 ml of cyclohexane and 550 ml of isopropanol, the water was azeotropically distilled off with the solvents. Final traces of water and solvents were removed in a water jet vacuum. The residue was recrystallized from acetone. 978 g of a colorless product containing 295.7 m vals of quaternary ammonium compound (QUAT) per 100 g of product were obtained.

EXAMPLE 5

Comparison of the antibacterial properties between
A: the compound of Example 4,
B: the compound of Example 3,
C: chlorhexidine, and
D: cetyl pyridinium chloride.

The destruction kinetics of the active compounds mentioned above against a typical cariogenic germ, Streptococcus mutans, were determined as follows using a quantitative suspension test:

Compounds A, B, C and D were dissolved in demineralized water (or aqueous solutions correspondingly diluted) so that the products were present in an active concentration of 500 ppm.

Quantities of 10 ml of these active solutions were inoculated with 0.1 ml of a test germ suspension containing $2 \times 10^8$ germs per ml and kept at room temperature (20° C.). 0.1 ml samples of these test preparations were taken after contact times of 0.5 minute, 1 minute and 2 minutes and spread using a spatula onto agar nutrient substrates both directly and also after dilution with demineralized water in a ratio of 1:10.

Figure 2:
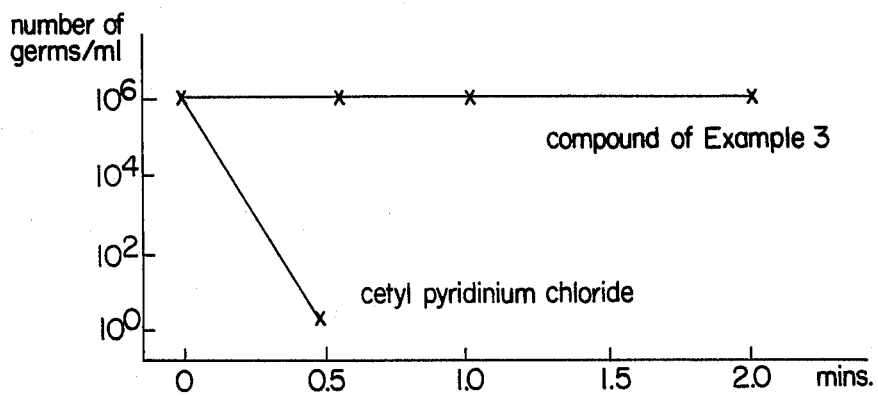

To neutralize the active compound after the contact time, both the dilution medium and also the nutrient agar contained a mixture of 3% by weight of Tween ®80 and 0.3% by weight of lecithin. After incubation for 2 days at 37° C., the infected nutrient substrates were counted and the number of surviving cells calculated therefrom. The results are shown in FIGS. 1 and 2.

The tests show that the compounds of formula I used in accordance with the invention do not destroy or inhibit Streptococcus mutans, an important caries germ, in times of practical relevance.

EXAMPLE 6

Clinical testing of the inhibition of plaque growth by the use of a mouthwash (a) containing no active ingredient,
(b) containing 0.1% by weight of chlorhexidine, and
(c) containing 0.1% by weight of the compound of Example 1.

The test involved 24 people in whom plaque growth had been brought to an equally low level by intensive brushing of the teeth. The test subjects were divided into three groups of 8 people and each of the three groups was given a mouthwash having the following composition for use three times a day:

| Composition % by weight | Group 3 (placebo) | Group 2 | Group 1 |
|---|---|---|---|
| Chlorhexidine | — | 0.1 | — |
| Compound of Example 1 (anhydrous) | — | — | 0.1 |
| Ethanol | 5.0 | 5.0 | 5.0 |
| Saccharin-Na | 0.01 | 0.01 | 0.01 |
| Aroma | 1.0 | 1.0 | 1.0 |
| Water (colored pale blue) | add to 100 | add to 100 | add to 100 |

No mechanical oral hygiene measures were taken during the test period of 4 days. Plaque growth was measured each morning in the form of the marginal line plaque index using Harrap's method, as described in Journal of Clinical Periodontology 1974, 1, pages 166–174.

The results of this test are shown in FIG. 3.

No staining by the compound according to the invention was observed either during the 4 day clinical test or after prolonged use.

No deterioration in the plaque-inhibiting effect by the proteins present in the saliva was observed. Testing of the compound of Example 3 produced the same result.

EXAMPLE 7

| Mouthwash | |
|---|---|
| Ethyl alcohol 96% by volume | 10.0% by weight |
| Tween ® 20 | 0.4% by weight |
| Aroma oil | 0.3% by weight |
| Sorbitol (70% aqueous solution) | 8.0% by weight |
| p-hydroxybenzoic acid methylester | 0.16% by weight |
| Compound of Example 4 | 0.05% by weight |
| Saccharin-sodium | 0.1% by weight |
| Dye q.s. | |
| Water (demineralized) | add to 100% by weight |

EXAMPLE 8 AND 9

| Toothpastes | | |
|---|---|---|
| Xerogel silica (Syloblanc ® 31) | 14 | 14% by weight |
| Aerogel silica (Syloid ® 244) | 6 | 6% by weight |
| Sorbitol (70% aqueous solution) | 25 | 25% by weight |
| Glycerin (86% aqueous solution) | 15 | 15% by weight |
| Polyethylene glycol 400 | 2 | 4% by weight |
| Hydroxyethyl cellulose (Cellosize ® WP 300 | 0.6 | 0.45% by weight |
| Fatty alcohol polyglycol ether (Dehydol ® TA 25) | 2.5 | 2.5% by weight |
| Compound of Example 4 | 0.3 | 0.3% by weight |
| Sodium fluoride | 0.22 | — % by weight |
| 1-hydroxyethane-1,1-diphosphonic acid disodium salt | — | 1.23% by weight |
| Titanium dioxide | 0.8 | 0.8% by weight |
| p-hydroxybenzoic acid methyl ester | 0.16 | 0.16% by weight |
| Aroma oil | 1.0 | 1.0% by weight |
| Saccharin-sodium | 0.2 | 0.2% by weight |
| Water (demineralized) | add to 100 | add to 100% by weight |

What is claimed is:

1. An oral and dental hygiene composition for the care of the oral cavity of a mammal comprising a quaternary ammonium compound of the formula

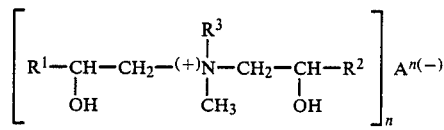

wherein;
$R^1$ is $C_8$–$C_{12}$-n-alkyl;
$R^2$ is hydrogen, —$CH_3$ or —$CH_2OH$;
$R^3$ is —$CH_3$ or —$CH_2CH(OH)$—$R_2$;
A is an inorganic or organic anion which forms a water-soluble salt with the quaternary ammonium compound which is physiologically compatible with the oral cavity of said mammal; and
n is the basicity of the anion A; and
wherein said quaternary ammonium compound is present in the hygiene composition in an amount effective to significantly inhibit the formation of dental plaque and ineffective to significantly inhibit microbial activity in the oral cavity.

2. The composition of claim 1, wherein said compound is present in an amount of from about 0.01% to about 2.0% by weight of the composition.

3. The composition of claim 2, wherein said compound is present in an amount of from about 0.03% to about 2.0% by weight of the composition.

4. The composition of claim 1, wherein $R^1$ in n-decyl.

5. The composition of claim 4, wherein A is fluoride.

6. The composition of claim 4, wherein $R^2$ is hydrogen and $R^3$ is $CH_3$ or 2-hydroxyethyl.

7. The composition of claim 6, wherein A is fluoride.

8. The composition of claim 6, wherein A is organophosphonate.

9. The composition of claim 8, wherein A is an organophosphonate anion of an organophosphonic acid of the formula II or III

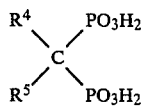

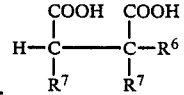

in which $R^4$ is alkyl containing from 1 to 6 carbon atoms, hydroxyl, amino, —$NHR^8$, wherein $R^8$ is alkyl containing from 1 to 3 carbon atoms, or —$CH_2$—COOH, —$CH_2PO_3H_2$, —$CH_2$—$CH_2$—$PO_3H_2$, —$CH(PO_3H_2)(OH)$ or —$CH_2$—CH—$(PO_3H_2)_2$; $R^5$ is hydrogen, alkyl containing from 1 to 6 carbon atoms or, where $R^4$ is amino or —$NHR^8$, forms a 5- to 7-membered azacycloalkane ring with the nitrogen atom and the central carbon atom; $R^6$ is —$PO_3H_2$, —$CR^7(COOH)(PO_3H_2)$, —$CR^7(PO_3H_2)_2$ or —$CR^7(COOH)$—$CH_2$—$PO_3H_2$; and $R^7$ is hydrogen, alkyl containing from 1 to 4 carbon atoms, or —$(CH_2)_{1-2}$—COOH.

10. The composition of claim 9, wherein $R^7$ is $CH_3$.

11. The composition of claim 4, wherein A is organophosphonate.

12. The composition of claim 11, wherein A is an organophosphonate anion of an organosphosphonic acid of the formula II or III

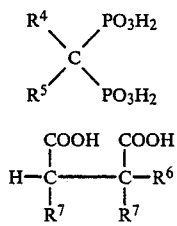

in which $R^4$ is alkyl containing from 1 to 6 carbon atoms, hydroxyl, amino group, —$NHR^8$, wherein $R^8$ is alkyl containing from 1 to 3 carbon atoms, or —$CH_2$—COOH, —$CH_2PO_3H_2$, —$CH_2$—$CH_2$—$PO_3H_2$, —$CH(PO_3H_2)(OH)$ or —$CH_2$—$CH(PO_3H_2)_2$; $R^5$ is hydrogen, alkyl containing from 1 to 6 carbon atoms or, where $R^4$ is amino or —$NHR^8$, forms a 5- to 7-membered azacycloalkane ring with the nitrogen atom and the central carbon atom; $R^6$ is —$PO_3H_2$, —$CR^7(COOH)(PO_3H_2)$, —$CR^7(PO_3H_2)_2$, or —$CR^7(COOH)$—$CH_2$—$PO_3H_2$; and $R^7$ is hydrogen, alkyl containing from 1 to 4 carbon atoms, or —$(CH_2)_{1-2}$—COOH.

13. The composition of claim 12, wherein $R^7$ is $CH_3$.

14. The composition of claim 1, wherein $R^2$ is hydrogen and $R^3$ is $CH_3$ or 2-hydroxyethyl.

15. The composition of claim 14, wherein A is fluoride.

16. The composition of claim 14, wherein A is organophosphonate.

17. The composition of claim 16, wherein A is an organophosphononate anion of an organophosphonic acid of the formula II or III

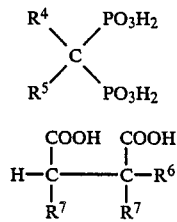

in which $R^4$ is alkyl containing from 1 to 6 carbon atoms, hydroxyl, amino, —$NHR^8$, wherein $R^8$ is alkyl containing from 1 to 3 carbon atoms, or —$CH_2$—COOH, —$CH_2PO_3H_2$, —$CH_2$—$CH_2$—$PO_3H_2$, —$CH(PO_3H_2)(OH)$ or —$CH_2$—CH—$(PO_3H_2)_2$; $R^5$ is hydrogen, alkyl containing from 1 to 6 carbon atoms or, where $R^4$ is amino or —$NHR^8$, forms a 5- to 7-membered azacycloalkane ring with the nitrogen atom and the central carbon atom; $R^6$ is —$PO_3H_2$, —$CR^7(COOH)(PO_3H_2)$, —$CR^7(PO_3H_2)_2$ or —$CR^7(COOH)$—$CH_2$—$PO_3H_2$; and $R^7$ is hydrogen, alkyl containing from 1 to 4 carbon atoms, or —$(CH_2)_{1-2}$—COOH.

18. The composition of claim 17, wherein $R^7$ is $CH_3$.

19. The composition of claim 1, wherein A is fluoride.

20. The composition of claim 1, wherein A is organophosphonate.

21. The composition of claim 20, wherein A is an organophosphonate anion of an organophosphonic acid of the formula II or III

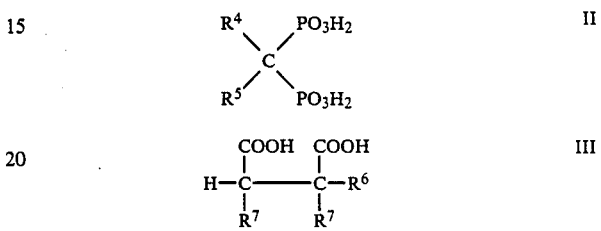

in which $R^4$ is alkyl containing from 1 to 6 carbon atoms, hydroxyl, amino, —$NHR^8$, wherein $R^8$ is alkyl containing from 1 to 3 carbon atoms, or —$CH_2$—COOH, —$CH_2PO_3H_2$, —$CH_2$—$CH_2PO_3H_2$, —$CH(PO_3H_2)(OH)$ or —$CH_2$—CH—$(PO_3H_2)_2$; $R^5$ is hydrogen, alkyl containing from 1 to 6 carbon atoms or, where $R^4$ is amino or —$NHR^8$, forms a 5- to 7-membered azacycloalkane ring with the nitrogen atom and the central carbon atom; $R^6$ is —$PO_3H_2$, —$CH^7(COOH)(PO_3H_2)$, —$CR^7(PO_3H_2)_2$ or —$CR^7(COOH)$—$CH_2$—$PO_3H_2$; and $R^7$ is hydrogen, alkyl containing from 1 to 4 carbon atoms, or —$(CH_2)_{1-2}$—COOH.

22. The composition of claim 21, wherein $R^7$ is $CH_3$.

23. The hygiene composition of claim 1 wherein the composition is a mouthwash further comprising an aqueous or aqueous-alcoholic solution, and wherein the quaternary ammonium compound is present in an amount of from about 0.03 to 0.3% by weight of the mouthwash.

24. The composition of claim 23, wherein $R^1$ is n-decyl.

25. The composition of claim 23, wherein $R^2$ is hydrogen and $R^3$ is $CH_3$ or 2-hydroxyethyl.

26. The composition of claim 23, wherein A is fluoride.

27. The mouthwash of claim 23, wherein A is an organophosphonate anion of an organophosphonic acid of the formula II or III

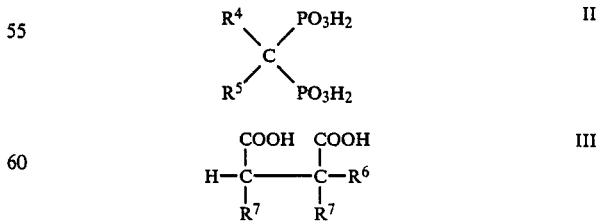

in which $R^4$ is alkyl containing from 1 to 6 carbon atoms, hydroxyl, amino, —$NHR^8$, wherein $R^8$ is alkyl containing from 1 to 3 carbon atoms, or —$CH_2$—COOH, —$CH_2PO_3H_2$, —$CH_2$—$CH_2$—$PO_3H_2$, —$CH(PO_3H_2)(OH)$ or —$CH_2$—CH—$(PO_3H_2)_2$; $R^5$ is hydrogen, alkyl containing from 1 to 6 carbon atoms or, where R is amino or —NHR[8] forms a 5- to 7-membered azacycloalkane ring with the nitrogen atom and the central carbon atom; R[6] is —PO$_3$H$_2$, —CH[7](COOH)(PO$_3$H$_2$), —CR[7](PO$_3$H$_2$)$_2$ or —CR[7](COOH)—CH$_2$—PO$_3$H$_2$; and R[7] is hydrogen, alkyl containing from 1 to 4 carbon atoms, or —(CH$_2$)$_{1-2}$—COOH.

28. The hygiene composition of claim 1 wherein the composition is a toothpaste further comprising a dental abrasive in an amount of from about 15 to about 40% by weight of the toothpaste, and a humectant in an amount up to about 50% by weight of the toothpaste, and wherein the quaternary ammonium compound is present in an amount of from about 0.1 to 0.5% by weight of the toothpaste.

29. The toothpaste of claim 28, wherein A is an organophosphonate anion of an organophosphonic acid of the formula II or III

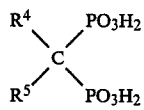

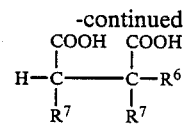

in which R[4] is alkyl containing from 1 to 6 carbon atoms, hydroxyl, amino, —NHR[8], wherein R[8] is alkyl containing from 1 to 3 carbon atoms, or —CH$_2$—COOH, —CH$_2$PO$_3$H$_2$, —CH$_2$—CH$_2$—PO$_3$H$_2$, —CH(PO$_3$H$_2$)(OH) or —CH$_2$—CH—(PO$_3$H$_2$)$_2$; R[5] is hydrogen, alkyl containing from 1 to 6 carbon atoms or, where R[4] is amino or —NHR[8], forms a 5- to 7-membered azacycloalkane ring with the nitrogen atom and the central carbon atom; R[6] is —PO$_3$H$_2$, —CH[7](COOH)(PO$_3$H$_2$), —CR[7](PO$_3$H$_2$) or —CR[7](COOH)—CH$_2$—PO$_3$H$_2$; and R[7] is hydrogen, alkyl containing from 1 to 4 carbon atoms, or —(CH$_2$)$_{1-2}$—COOH.

30. The composition of claim 29, further comprising an ethoxylated sorbitan fatty acid ester, an ethoxylated glycerol fatty acid ester, an alkyl glucoside, or a fatty alcohol polyglycol ester.

31. The composition of claim 28, wherein the polish comprises a particulate xerogel silicate, a hydrogel silica, a precipitated silica, an aluminum oxide trihydrate, or a particulate -aluminum oxide.

32. The composition of claim 28, wherein R[1] is n-decyl.

33. The composition of claim 28, wherein R[2] is hydrogen and R[3] is CH$_3$ or 2-hydroxyethyl.

34. The composition of claim 28, wherein A is fluoride.

* * * * *